United States Patent
Bal

(10) Patent No.: US 11,096,634 B2
(45) Date of Patent: Aug. 24, 2021

(54) SCATTER CORRECTION BASED ON ENERGY RESPONSE

(71) Applicant: Siemens Medical Solutions USA, Inc., Malvern, PA (US)

(72) Inventor: Harshali Bal, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 16/946,304

(22) Filed: Jun. 16, 2020

(65) Prior Publication Data

US 2021/0059617 A1 Mar. 4, 2021

Related U.S. Application Data

(60) Provisional application No. 62/891,560, filed on Aug. 26, 2019.

(51) Int. Cl.
*A61B 6/03* (2006.01)
*A61B 6/00* (2006.01)
*G01T 1/29* (2006.01)

(52) U.S. Cl.
CPC .............. *A61B 6/037* (2013.01); *A61B 6/481* (2013.01); *A61B 6/5205* (2013.01); *G01T 1/2964* (2013.01); *G01T 1/2985* (2013.01)

(58) Field of Classification Search
CPC ....... A61B 6/037; A61B 6/481; A61B 6/5205; A61B 6/4417; A61B 6/5282; A61B 6/032; G01T 1/2964; G01T 1/2985
See application file for complete search history.

(56) References Cited

U.S. PATENT DOCUMENTS

| | | | |
|---|---|---|---|
| 7,381,959 B2 * | 6/2008 | Manjeshwar | G01T 1/2985 250/363.03 |
| 2021/0124067 A1 * | 4/2021 | Aykac | A61B 6/582 |

OTHER PUBLICATIONS

Popescu, Lucretiu M. et al., "PET Energy-based Scatter Estimation and Image Reconstruction with Energy-dependent Corrections", Phys. Med. Biol., vol. 51, 2006, (pp. 2919-2937, 23 total pages).

\* cited by examiner

*Primary Examiner* — Michael C Bryant

(57) ABSTRACT

Systems and methods include acquisition of data representing true coincidences and scatter coincidences detected by the plurality of detectors, allocation of the data into respective ones of a plurality of energy ranges, determination of a baseline response associated with each of a subset of the plurality of energy ranges, generation of data representing expected true coincidences associated with each of the subset of the plurality of energy ranges based on the data allocated to each of the subset of the plurality of energy ranges and the baseline response associated with each of the subset of the plurality of energy ranges, determination of a raw scatter estimate based on the data representing expected true coincidences associated with each of the subset of the plurality of energy ranges and the data allocated to each of the subset of the plurality of energy ranges, and reconstruction of an image based on the raw scatter estimate and the data representing true coincidences and scatter coincidences.

20 Claims, 10 Drawing Sheets

SCATTER CORRECTION BASED ON ENERGY RESPONSE

CROSS-REFERENCE TO RELATED APPLICATIONS

The present application claims benefit of and priority to U.S. Provisional Patent Application Ser. No. 62/891,560, filed Aug. 26, 2019, for all purposes.

BACKGROUND

According to conventional positron-emission-tomography (PET) imaging, a radiopharmaceutical tracer is introduced into a patient body typically via arterial injection. Radioactive decay of the tracer generates positrons which eventually encounter electrons and are annihilated thereby. Annihilation produces two photons which travel in approximately opposite directions.

A ring of detectors surrounding the body detects the emitted photons, identifies "coincidences", and reconstructs PET images based on the identified coincidences. A coincidence is identified when two detectors disposed on opposite sides of the body detect the arrival of two photons within a particular coincidence time window. Because the two "coincident" photons travel in approximately opposite directions, the locations of the two detectors determine a Line-of-Response (LOR) along which an annihilation event may have occurred.

A "true" coincidence represents the detection of two coincident photons which arose from a single annihilation event located on a LOR between the two detectors. A "random" coincidence represents two coincident photons which did not arise from the same annihilation event. A "scatter" coincidence is a type of true coincidence in which two coincident photons originated from the same annihilation event but the annihilation event was not located along the LOR of the two detectors because one or both of the photons interacted and scattered within the body.

Conventional PET scanners detect all coincidences without regard to whether the coincidences are true, random or scatter coincidences. Since only the true coincidences represent spatial information regarding the distribution of the tracer within the body, random and scatter coincidences should be addressed prior to and/or during image reconstruction. Software and/or hardware-based approaches can be used to estimate random coincidences and to subtract the random coincidences from the detected coincidences. Model-based scatter correction uses a Computed Tomography (CT)-derived attenuation map to estimate and correct for Compton scatter. Model-based scatter correction therefore requires the time and resources of a separate prior CT scan and is prone to registration errors.

Systems are desired to perform PET scatter correction without requiring an attenuation map.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments estimate scatter coincidences within detected PET coincidence events based on a baseline energy response of a PET imaging system. The baseline energy response is obtained from a source of unscattered annihilation photons. According to some embodiments, the baseline response for several low-energy energy ranges is used to determine a proportion of expected true coincidences for each low-energy energy range, and to estimate that the remaining coincidences within each low-energy energy range are scatter coincidences. The estimated scatter coincidences are combined to determine a raw scatter estimate.

The raw scatter estimate may be supplemented in some embodiments by an estimation of scatter coincidences within high-energy energy ranges. These high-energy scatter coincidences may be estimated based on the estimated scatter coincidences within a higher-energy range of the low-energy energy ranges. Coefficients for refining the raw scatter estimate and the high-energy scatter estimate may be previously-determined from a calibration scan which allows scatter to be determined from experimental data.

Generally, a PET detector includes one or more scintillation elements and one or more electrical transducers. The scintillation elements create photons with the energy of a few electron volts (eV) in response to receiving the 511 keV photons which result from annihilation events. The electrical transducers convert the low-energy photons created by the scintillation elements to electrical signals. According to some embodiments, the electrical transducers may comprise, for example, SiPMs, PMTs, or semiconductor-based detectors.

The coincidences detected over a period of time (i.e., a frame) may be stored in a sinogram. A sinogram is a data array of the angle versus the displacement of each LOR of each detected coincidence. A sinogram includes one row containing the LOR for a particular azimuthal angle φ. Each of these rows corresponds to a one-dimensional parallel projection of the tracer distribution at a different coordinate. A sinogram stores the location of the LOR of each coincidence such that all the LORs passing through a single point in the volume trace a sinusoid curve in the sinogram.

A sinogram may represents each coincidence by its LOR, energy level, the time at which the coincidence occurred, and other information. According to time-of-flight (TOF) PET imaging, also recorded is the difference between the arrival times of the two photons whose detection resulted in the detected coincidence. This difference may be used to more accurately estimate a particular position along the LOR at which the corresponding annihilation event occurred.

Figure 1A:
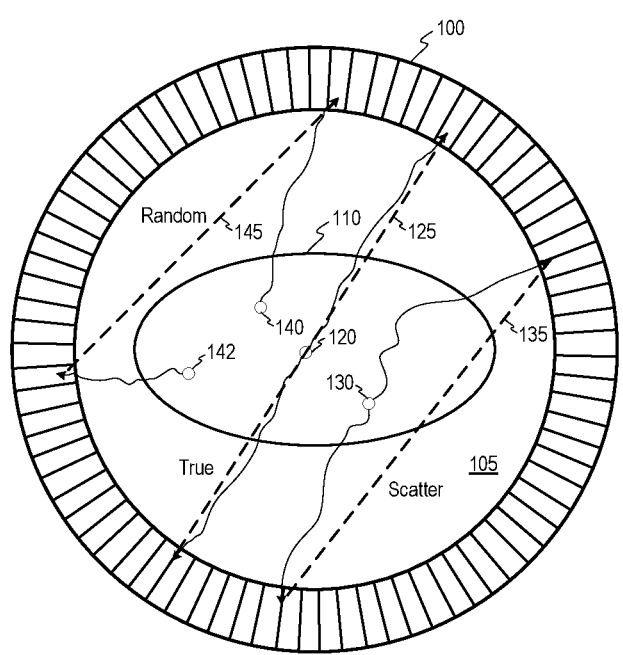
FIGS. 1a and 1b illustrate detection of coincidence events according to some embodiments.
Figure 1B:
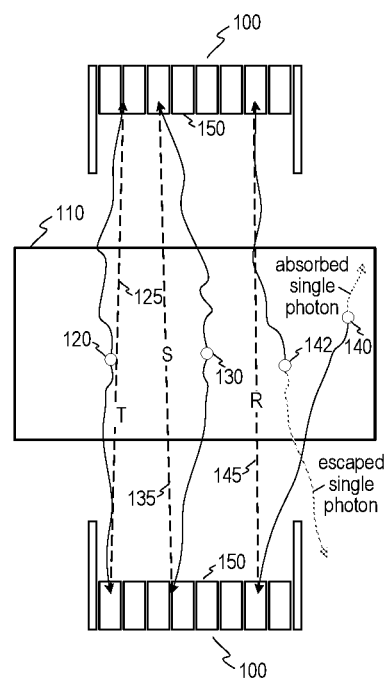

FIG. 1a and FIG. 1b illustrate detection of coincidences according to some embodiments. FIG. 1a is an axial view of bore 105 of detector ring 100 and imaging subject 110 disposed therein. Imaging subject 110 may comprise a human body, a phantom, or any other suitable subject. FIG. 1b is a transaxial view of detector ring 100 and body 110 of FIG. 2a. Detector ring 100 is composed of an arbitrary number (eight in this example) of adjacent and coaxial rings of detectors 150 in the illustrated example. Each detector 150 may comprise any number of scintillator crystals and electrical transducers.

Annihilation events 120, 130, 140 and 142 are assumed to occur at various locations within subject 110. As described above, an injected tracer generates positrons which are annihilated by electrons to produce two 511 keV gamma photons which travel in approximately opposite directions. Each annihilation event represented in FIG. 1a and FIG. 1b results in the detection of a coincidence. True coincidences represent valid image data, while scatter and random coincidences represent noise.

A coincidence is detected when a pair of detectors receive two gamma photons within the coincidence time window, as determined based on the calculated arrival times of the two gamma photons at their respective detectors. Event 120 is associated with a true coincidence because event 120 resulted in two gamma photons which were received within the coincidence time window and because the position of annihilation event 120 lies on LOR 125 connecting the detector positions at which the two gamma photons were received.

Event 130 is associated with a scatter coincidence because, even though the two gamma photons resulting from event 130 were detected within the coincidence time window, the position of annihilation event 130 does not lie on LOR 135 connecting the two photon positions. This may be due to Compton (i.e., inelastic) or Coherent (i.e., elastic) scatter resulting in a change of direction of at least one of the two gamma photons within subject 110.

Events 140 and 142 are two separate annihilation events which result in detection of a random coincidence. In the present example, one of the photons generated by event 140 is absorbed in body 210 and one of the photons generated by event 142 escapes detection by any detector 150 of detector ring 100. The remaining photons happen to be detected within the coincidence time window, even though no annihilation event occurred on LOR 145 connecting the positions at which the coincident photons were received.

Since only the true unscattered coincidences indicate locations of annihilation events, random coincidences and scatter coincidences are often subtracted from or otherwise used to correct acquired PET data during reconstruction of a PET image.

Figure 2:
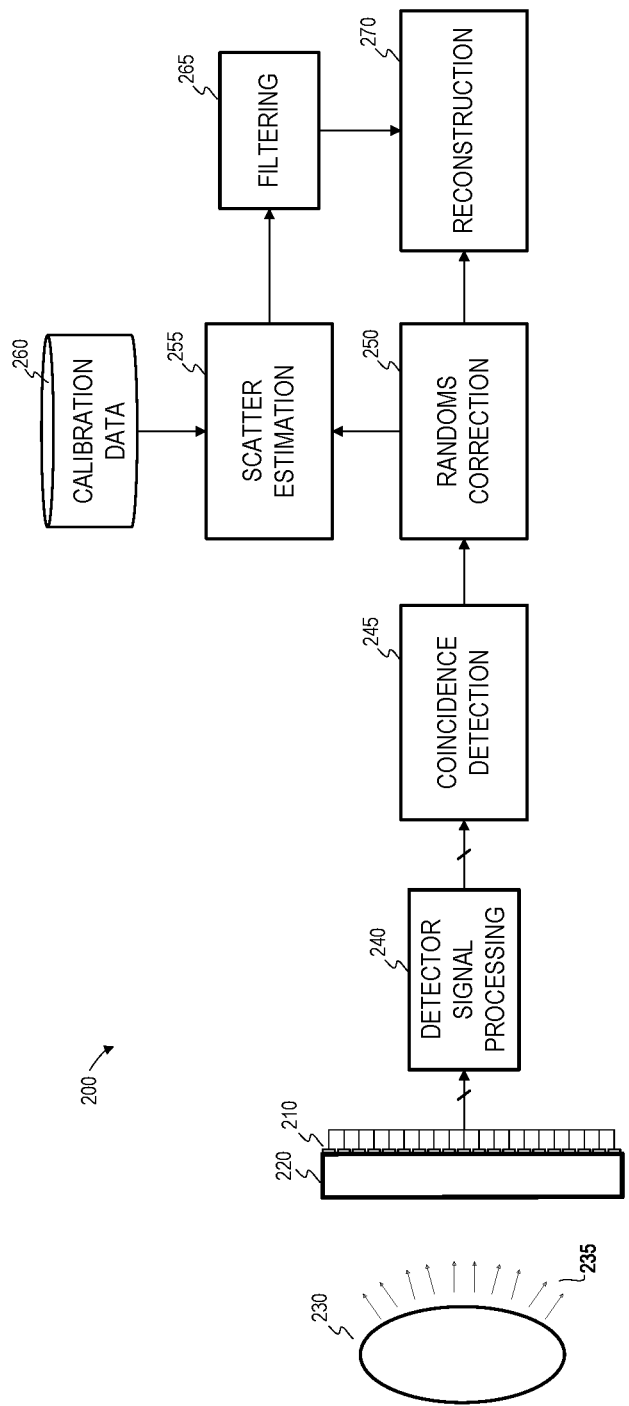
FIG. 2 is a block diagram of a system to estimate and correct for scatter coincidences according to some embodiments.

FIG. 2 illustrates imaging system 200 according to some embodiments. Each component of system 200 may be implemented by any suitable combination of hardware and software. One or more components may be implemented by a single software application in some embodiments.

System 200 includes detectors 210 of a portion of a detector ring and corresponding scintillator 220. Scintillator 220 may be pixelated or monolithic (as shown). Embodiments are not limited to scintillator-based detectors. Direct conversion detectors (e.g., CZT and TlBr) may also be used in conjunction with some embodiments.

Detectors 210 detect gamma photons 235 emitted from volume 230. Systems for facilitating the emission of gamma photons from a volume are known in the art, and in particular with respect to the PET imaging described herein. As described above, scintillator 220 receives the gamma photons 235 and emits light photons in response. Detectors 210 receive the light photons emitted by scintillator 220 and each detector 210 generates electrical signals based on the energy of the received photons and its own characteristic photoelectric response profile.

Detector signal processing unit 240 receives the electrical signals generated by each detector 210 and performs signal processing to, for example, determine whether a signal represents a photon detection event, perform signal unpiling by pile-up rejection, determine an event energy, and determine an event time. Detector signal processing unit 240 may perform any suitable functions and exhibit any suitable implementations.

During a give frame duration, coincidence detection unit 245 receives all photon detection events which pass energy qualification (e.g., between 435 and 585 keV) from all detectors of the detector ring. Based on the reception time of each photon detection event, unit 245 identifies pairs of photon detection events which were received within a coincidence time window and determines that each such pair corresponds to a coincidence having an associated LOR and energy. Coincidence detection unit 245 may also determine, for each pair of photon detection events, a TOF value representing a difference in the reception time of the photon detection events. Data representing each detected coincidence is stored in a sinogram as is known in the art.

Randoms correction unit 250 attempts to remove randoms coincidences from the detected coincidence sinogram. For example, one current hardware-based approach involves delaying one of the detected singles events. Undelayed logic detects all coincidences along all LORs as described above. Additional delayed logic delays one input channel by, for example, a few tens of nanoseconds (e.g., 5× the coincidence window) and then performs coincidence detection. As a result, the delayed logic does not detect any actually-true coincidences as coincident. To correct for random coincidences, and for each LOR represented in the sinogram, the coincidences detected by the delayed logic are subtracted from those detected by the undelayed logic.

Scatter estimation unit 255 may estimate scatter coincidences based on a randoms-corrected (i.e., net trues) sinogram according to some embodiments. Generally, as will be described in detail below, scatter estimation unit 255 may estimate scatter coincidences within the sinogram based on a baseline energy response of PET imaging system 200. Data indicating the baseline energy response may be stored in calibration data 260. Calibration data 260 may also store calibration factors for refining scatter estimates based on experimental data.

A sinogram of the estimated scatter coincidences may be subjected to filtering 265. Reconstruction unit 270 executes a reconstruction algorithm to reconstruct an image based on the filtered sinogram and on the randoms-corrected sinogram output from randoms correction unit 250.

Figure 3A:
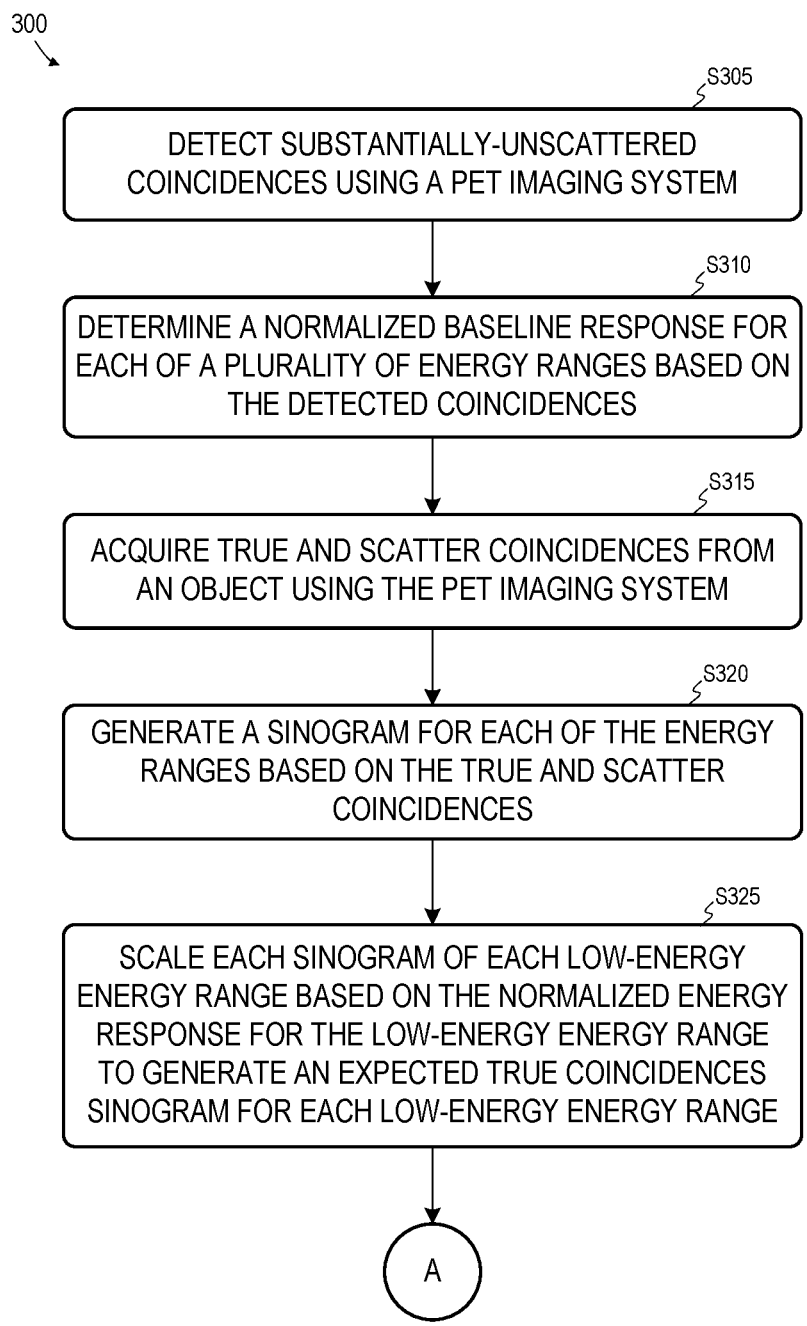
FIGS. 3a and 3b comprise a flow diagram of a process to estimate and correct for scatter coincidences according to some embodiments.
Figure 3B:
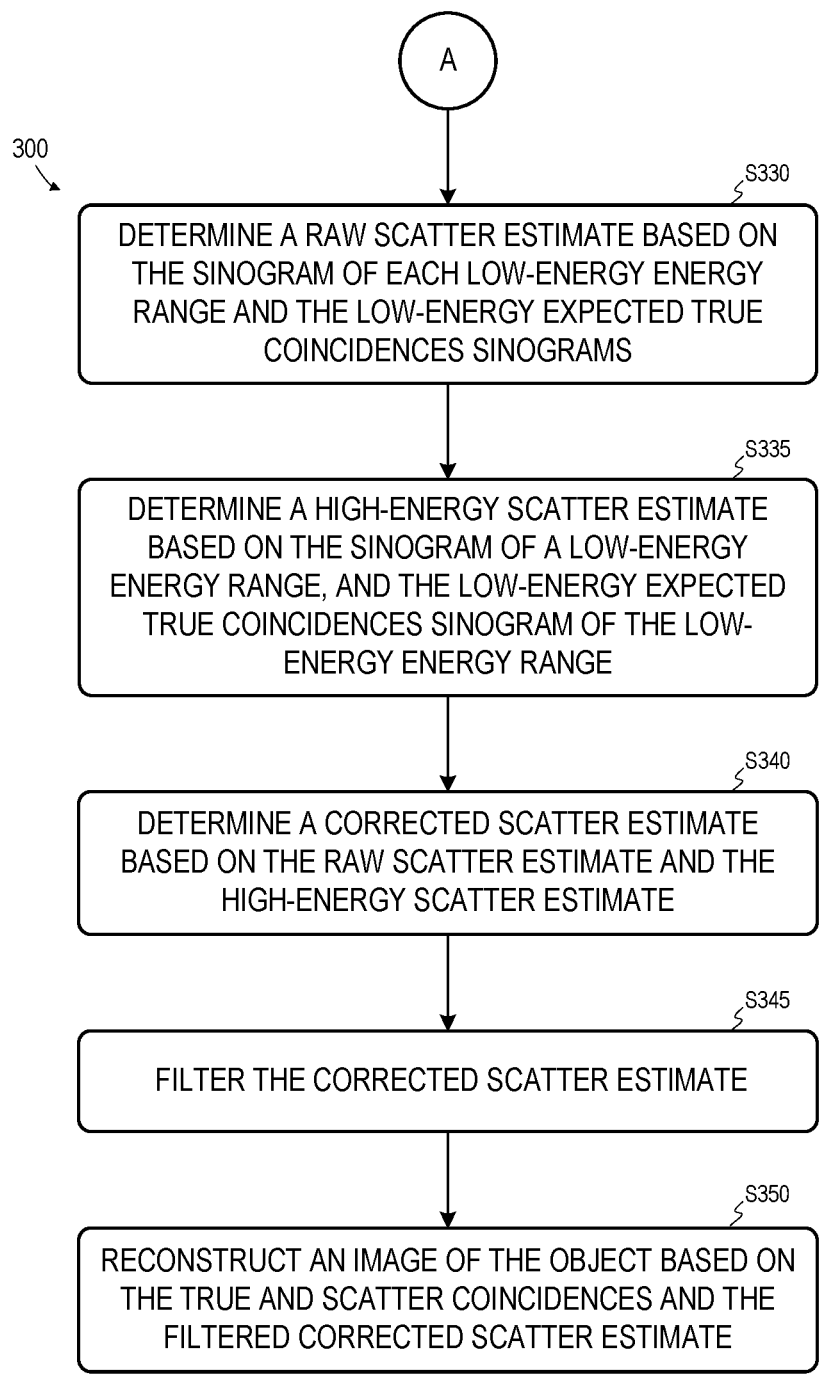

FIGS. 3a and 3b comprise a flow diagram of process 300 to perform scatter correction on coincidence data according to some embodiments. Flow diagram 300 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processing cores, and processor threads. Embodiments are not limited to the examples described below.

Initially, at S305, coincidences are detected using a PET imaging system as is known in the art. The detected coincidences are substantially unscattered, that is, the detected coincidences include a negligible amount of scatter coincidences. According to some embodiments of S305, a line source of gamma photons (e.g., Fludeoxyglucose or Germanium inside a stainless steel rod) is placed in the bore of a PET detector ring, resulting coincidences are detected over a period of time, and data representing the coincidences is stored in a sinogram.

A normalized baseline response is determined at S310 for each of a plurality of energy ranges based on the detected coincidences. For example, a qualifying energy spectrum (e.g., 435 to 585 keV) is divided into 16 equal energy ranges. The energy of each coincidence detected at S305 is determined and the number of coincidences falling into each energy range is determined. The numbers associated with each energy range are then normalized to the peak number.

Figure 4:
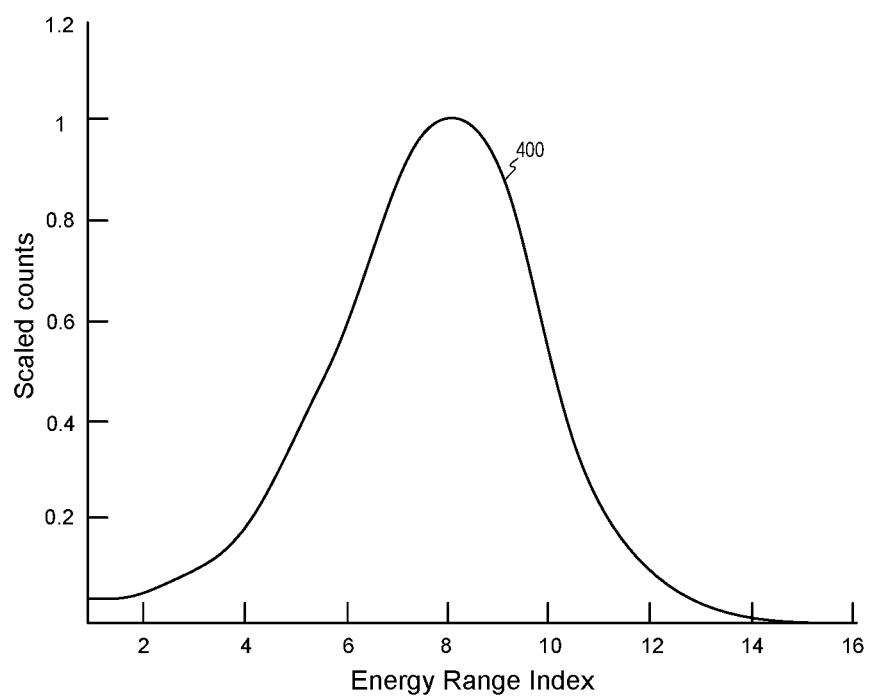
FIG. 4 is a graph of a baseline energy response of a PET imaging system to substantially-unscattered coincidence events according to some embodiments.

FIG. 4 illustrates normalized baseline response 400 determined at S310 according to some embodiments. Each energy range is associated with a scaled count value, where the peak value is 1.

An object is imaged at S315 as is known in the art of PET imaging to detect coincidences over time. Imaging may include injection of a radionuclide tracer into the object and detection of resulting coincidences as described above. It will be assumed that the coincidences are corrected for randoms, resulting in a sinogram reflecting true and scatter coincidences (i.e., "net" trues).

Figure 5:
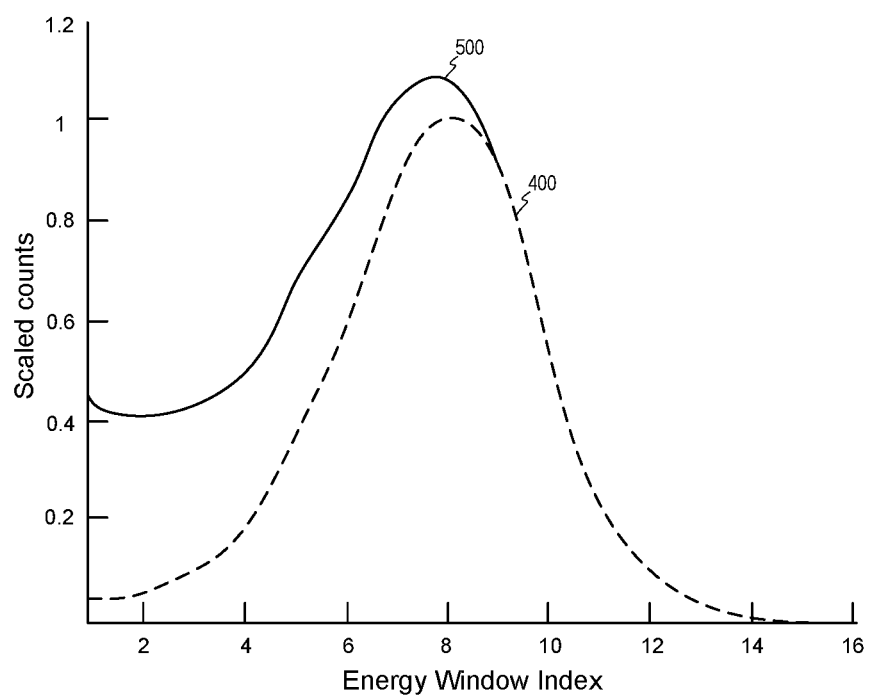
FIG. 5 is a graph of an energy response of a PET imaging system to coincidence events according to some embodiments.

The coincidences of the sinogram are binned based on energy ranges as described with respect to S310. FIG. 5 illustrates profile 500 of normalized coincidence counts per energy range for the coincidences acquired at S315 in one example. As shown, the relative number of coincidences in the lower-energy energy ranges is greater than that of the baseline (i.e., unscattered) response. The difference in profiles 400 and 500 may represent scatter coincidences, particularly since scatter coincidences tend to exhibit lower energies than true coincidences.

Figure 6:
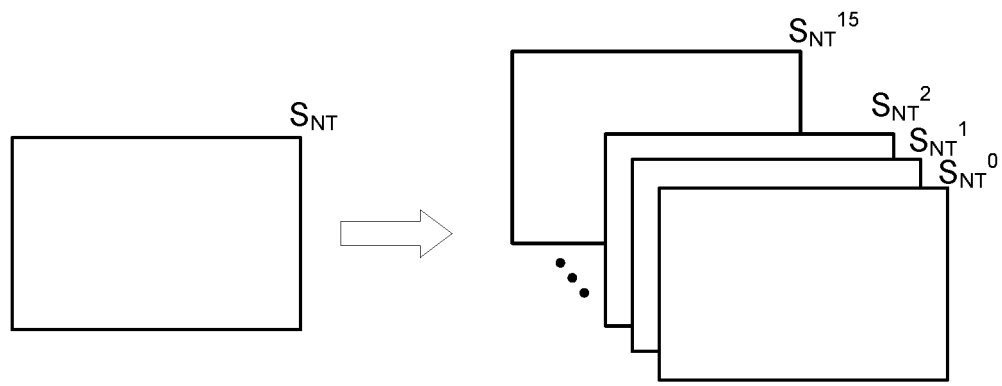
FIG. 6 illustrates generation of energy range-specific sinograms according to some embodiments.

Sinograms are generated for each energy range (i.e., bin) based on the coincidences associated with the energy range. For example, FIG. 6 illustrates sinogram $S_{NT}$ of the true and scatter coincidences acquired at S315. Each coincidence of sinogram $S_{NT}$ is apportioned into one of sixteen sinograms $S_{NT}^0$ to $S_{NT}^{15}$ based on the energy of the coincidence, where each of sinograms $S_{NT}^0$ to $S_{NT}^{15}$ corresponds to one of energy ranges 0 through 15.

Figure 7:
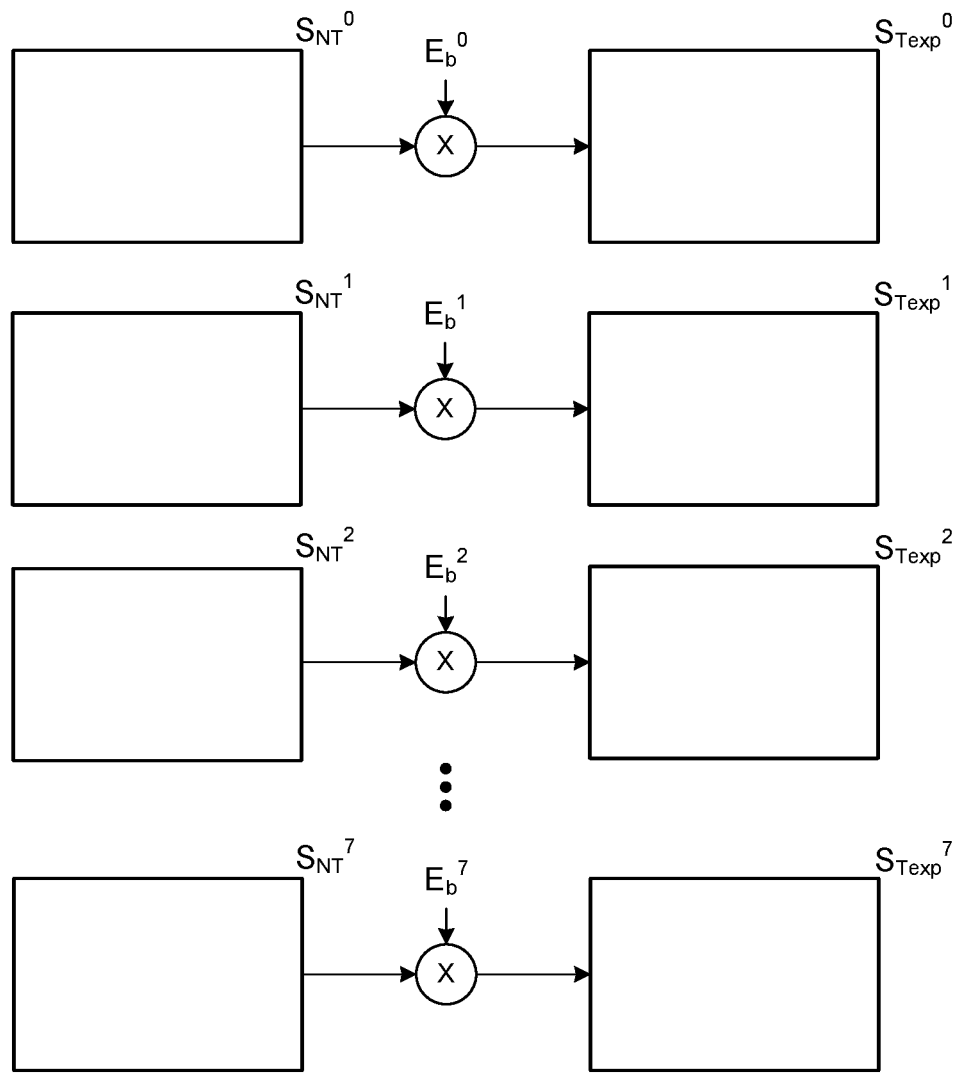
FIG. 7 illustrates determination of energy range-specific expected true coincidences sinograms according to some embodiments.
Figure 8:
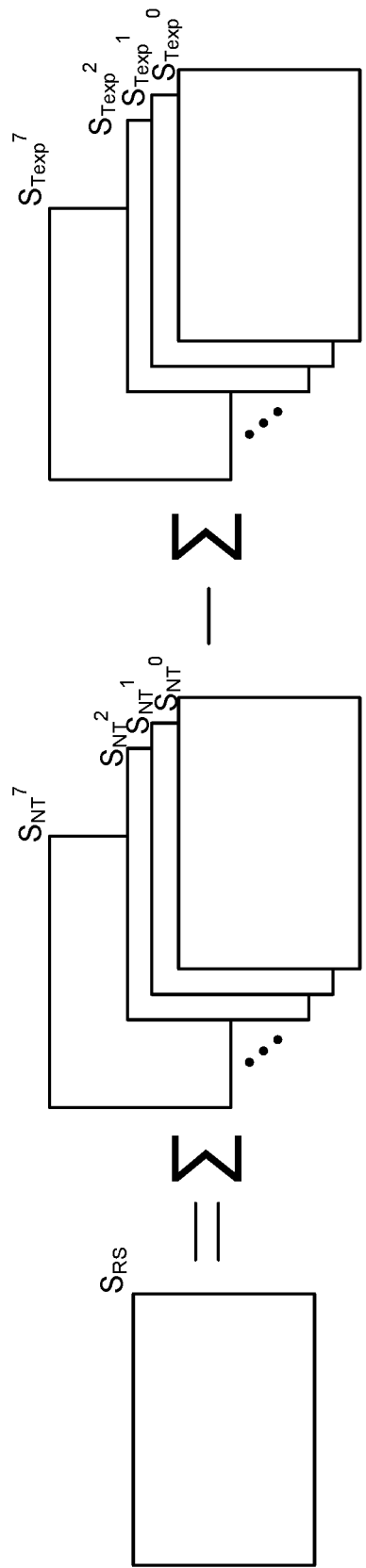
FIG. 8 illustrates determination of a raw scatter estimate sinogram according to some embodiments.

Next, at S325, each sinogram associated with a low-energy energy range is scaled based on the normalized energy response associated with the energy range. For example, in a case that energy ranges 0 through 7 are considered to be "low-energy" ranges, each of sinograms $S_{NT}^0$ through $S_{NT}^7$ is multiplied by the scaling factor associated with its associated energy range by profile 400 of FIG. 4. FIG. 7 illustrates this operation according to some embodiments, in which the scaling factor of energy range N (i.e., the y-coordinate of profile 400 associated with energy range index N) is depicted as $E_b^N$. Scaling of each sinogram $S_{NT}^0$ through $S_{NT}^7$ at S325 results in expected true coincidences sinograms $S_{Texp}^0$ through $S_{Texp}^7$, each of which corresponds to an energy range.

A raw scatter estimate is determined at S330 based on the sinogram of each low-energy energy range and the expected true coincidences sinograms generated at S325. FIG. depicts the determination of raw scatter estimate $S_{RS}$ at S330 according to some embodiments. As shown, expected true coincidences sinograms $S_{Texp}^0$ through $S_{Texp}^7$ are combined (e.g., summed) and the resulting sinogram is subtracted from a combination (e.g., sum) of low-energy energy range sinograms $S_{NT}^0$ through $S_{NT}^7$.

Figure 9:
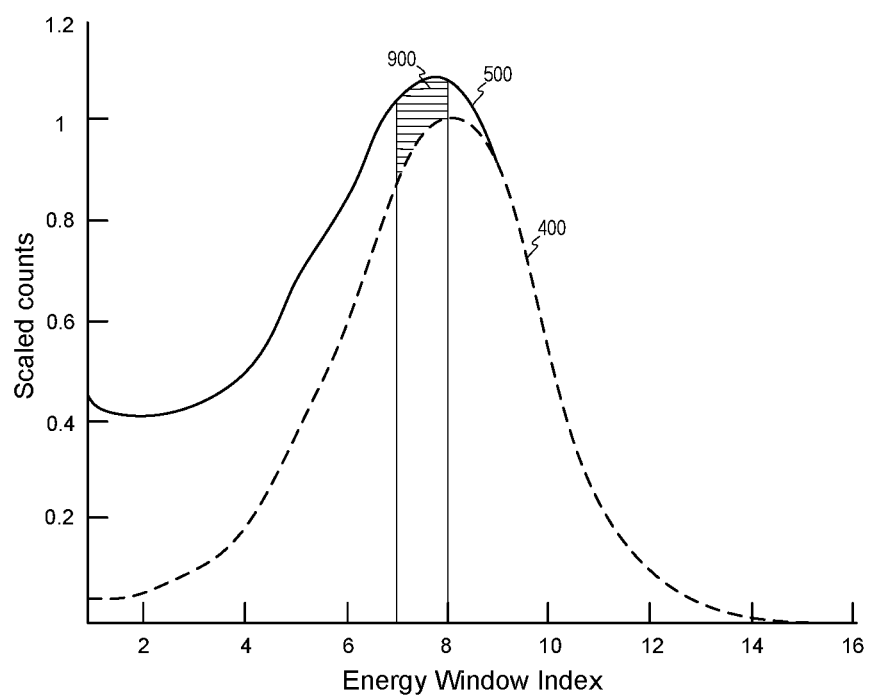
FIG. 9 illustrates estimation of high-energy scatter according to some embodiments.

According to some embodiments, a high-energy scatter estimate (e.g., $S_{HES}$) is determined at S335 to estimate the scatter coincidences present in the higher-energy energy ranges of net trues sinogram $S_{NT}$. Determination of the high-energy scatter estimate may comprise identifying a sinogram associated with a higher energy range of the low-energy energy ranges (e.g., $S_{NT}^7$) and the corresponding expected true coincidences sinogram (e.g., $S_{Texp}^7$). The high-energy scatter estimate may then be calculated as the difference between the two sinograms, representing scatter depicted by shaded area 900 between profiles 400 and 500 of FIG. 9.

A corrected scatter estimate (e.g., $S_{Corr}$) is determined at S340 based on the raw scatter estimate and the high-energy scatter estimate. For example, $S_{Corr}=S_{RS}+S_{HES}$. According to some embodiments, determination of the corrected scatter estimate may comprise multiplying one or both of the raw scatter estimate and the high-energy scatter estimate by a corresponding experimentally-derived coefficient and summing the products, such as: $S_{Corr}=A^1*S_{RS}+A_2*S_{HES}$. Some embodiments may employ an additional correction factor based on a sinogram of all the high-energy energy level coincidences (e.g., $S_{HET}$) as follows: $S_{Corr}=A^1*S_{RS}+A_2*S_{HES}-A_3*S_{HET}$.

The corrected scatter estimate is filtered at S345 to reduce a noise profile thereof. According to some embodiments of S345, a three-dimensional Gaussian filter is applied to sinogram $S_{Corr}$. Next, at S350, an image of the object is reconstructed based on the true and scatter coincidences (i.e., the net trues) acquired at S315 and the filtered corrected scatter estimate. Accordingly, S350 may comprise execution of a reconstruction algorithm which takes a net true sinogram and an estimated scatter sinogram as input.

As mentioned above, some PET imaging systems provide, for each coincidence, a TOF value representing a difference in the reception time of the photon detection events of the coincidence. The TOF value may be used to localize the position of the annihilation event along the LOR of the coincidence. According to some embodiments, the TOF values may provide an additional dimension for binning sinogram data for scatter correction.

For example, according to some embodiments, the net trues data acquired S315 also includes TOF flight data for each coincidence. This data is binned into respective TOF ranges to generate a sinogram for each TOF bin. To address the sparsity inherent to TOF data, and in the case of 33 TOF bins, 33 sinograms are generated by summing the sinograms of each TOF bin except for one of the 33 bins. A $34^{th}$ sinogram is also generated consisting of the summed sinograms of all 33 TOF bins. Then, according to some embodiments, steps S320 through S340 are performed independently for each of the 34 sinograms. The resulting 34 corrected scatter estimates are summed prior to filtering at S345.

Figure 10:
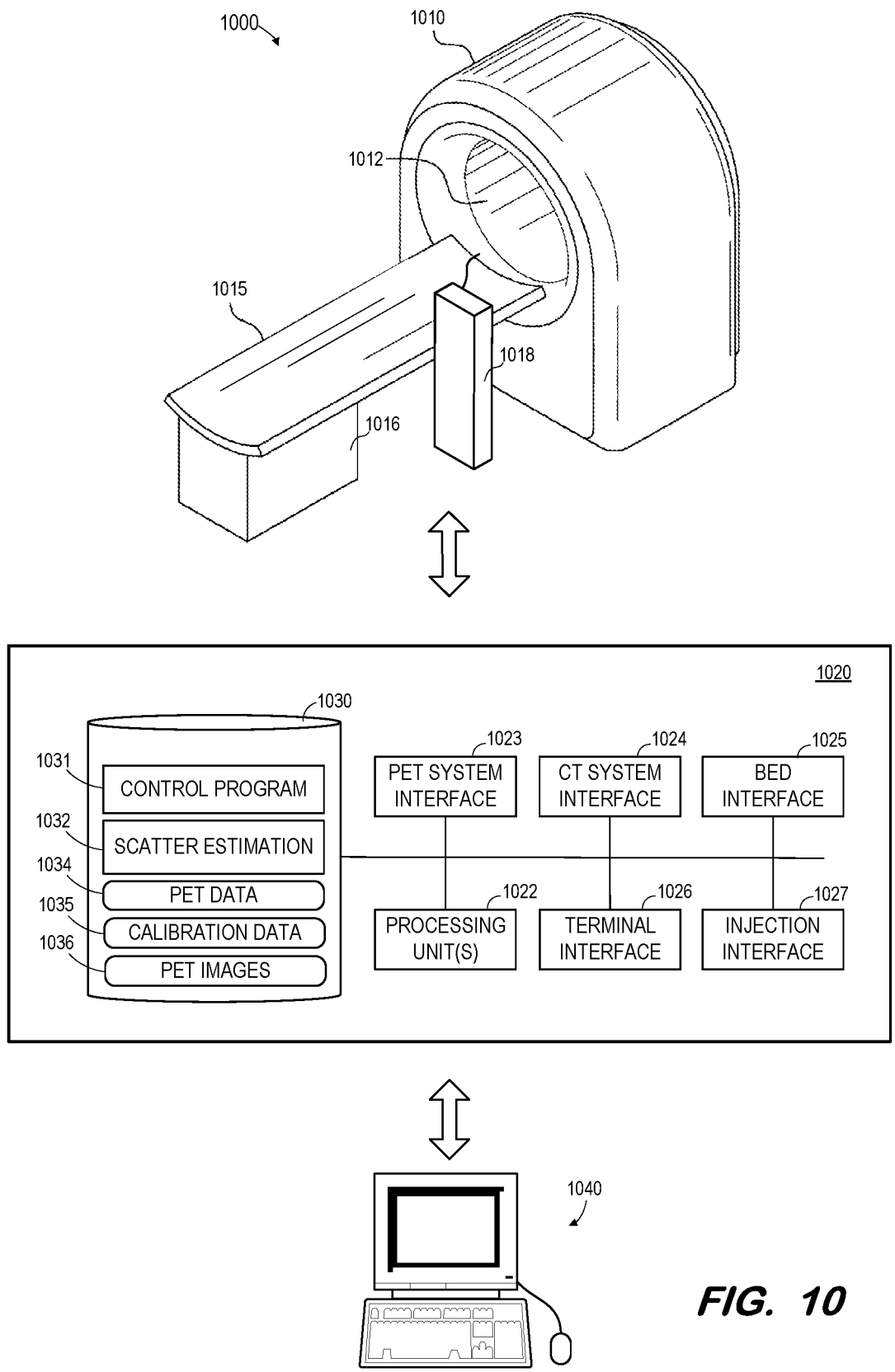
FIG. 10 is a block diagram of a PET imaging system according to some embodiments.

FIG. 10 illustrates PET/CT system 1000 to execute one or more of the processes described herein. Embodiments are not limited to system 1000.

System 1000 includes gantry 1010 defining bore 1012. As is known in the art, gantry 1010 houses PET imaging components for acquiring PET image data and CT imaging components for acquiring CT image data. The CT imaging components may include one or more x-ray tubes and one or more corresponding x-ray detectors as is known in the art.

The PET imaging components may include any number or type of detectors in any configuration as is known in the art. Generally, a detector includes one or more scintillation elements and one or more electrical transducers. Injection system 1018 may operate to deliver calibrated injections of fluorodeoxyglucose, iodine, or other radiopharmaceuticals to a patient before and/or during a PET scan. In some embodiments, injection system 1018 is incorporated into gantry 1010. Injection system 1018 may support a wired or wireless communications link with control system 1020 for receiving information specifying dosage, injection protocol and scan delay.

Bed 1015 and base 1016 are operable to move a patient lying on bed 1015 into and out of bore 1012 before, during and after imaging. In some embodiments, bed 1015 is configured to translate over base 1016 and, in other embodiments, base 1016 is movable along with or alternatively from bed 1015.

Movement of a patient into and out of bore 1012 may allow scanning of the patient using the CT imaging elements and the PET imaging elements of gantry 1010. Such scanning may proceed based on scanning parameters such as scan ranges and corresponding scanning speeds. Bed 1015 and base 1016 may provide continuous bed motion and/or step-and-shoot motion during such scanning according to some embodiments.

Control system 1020 may comprise any general-purpose or dedicated computing system. Accordingly, control system 1020 includes one or more processing units 1022 configured to execute processor-executable program code to cause system 1020 to operate as described herein, and storage device 1030 for storing the program code. Storage device 1030 may comprise one or more fixed disks, solid-state random-access memory, and/or removable media (e.g., a thumb drive) mounted in a corresponding interface (e.g., a USB port).

Storage device 1030 stores program code of control program 1031. One or more processing units 1022 may execute control program 1031 to, in conjunction with PET system interface 1023, bed interface 1025, and injection interface 1027, control hardware elements to inject a radiopharmaceutical into a patient, move the patient into bore 1012 past PET detectors of gantry 1010, and detect coincidences occurring within the patient. The detected events may be stored in storage 1030 as PET data 1034, which may comprise raw (i.e., list-mode) data and/or sinograms.

Storage device 1030 also includes scatter estimation program 1032 for estimating scatter as described herein. As described, such estimation utilizes previously-acquired calibration data 1035, which may include normalized baseline response data and calibration coefficients. In this regard, control program 1031 may also be executed to reconstruct PET images 1036 based on PET data 1034 and the estimated scatter using any suitable reconstruction algorithm that is or becomes known.

PET images 1036, CT images and/or estimated scatter may be transmitted to terminal 1040 via terminal interface 1026. Terminal 1040 may comprise a display device and an input device coupled to system 1020. Terminal 1040 may display the PET images, CT images, and/or estimated scatter. Terminal 1040 may receive user input for controlling display of the data, operation of system 1000, and/or the processing described herein. In some embodiments, terminal 1040 is a separate computing device such as, but not limited to, a desktop computer, a laptop computer, a tablet computer, and a smartphone.

Each component of system 1000 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   a positron emission tomography scanner comprising a plurality of detectors; and
   a processing unit to:
   acquire data representing true coincidences and scatter coincidences detected by the plurality of detectors;
   allocate the data into respective ones of a plurality of energy ranges;
   determine a baseline response associated with each of a subset of the plurality of energy ranges;
   generate data representing expected true coincidences associated with each of the subset of the plurality of energy ranges based on the data allocated to each of the subset of the plurality of energy ranges and the baseline response associated with each of the subset of the plurality of energy ranges;
   determine a raw scatter estimate based on the data representing expected true coincidences associated with each of the subset of the plurality of energy ranges and the data allocated to each of the subset of the plurality of energy ranges; and
   reconstruct an image based on the raw scatter estimate and the data representing true coincidences and scatter coincidences.

2. A system according to claim 1, the processing unit to:
   determine a high-energy scatter estimate based on data representing expected true coincidences associated with a highest-energy subset of the plurality of energy ranges and the data allocated to the highest-energy subset of the plurality of energy ranges,
   wherein reconstruction of the image comprises reconstruction of the image based on the raw scatter estimate, the high-energy scatter estimate, and the data representing true coincidences and scatter coincidences.

3. A system according to claim 2, the processing unit to:
   determine a corrected scatter estimate based on the raw scatter estimate and the high-energy scatter estimate; and
   filter the corrected scatter estimate, wherein reconstruction of the image comprises reconstruction of the image based on the filtered corrected scatter estimate and the data representing true coincidences and scatter coincidences.

4. A system according to claim 1, wherein the baseline response associated with each of the subset of the plurality of energy ranges comprises normalized counts of true coincidences for each of the subset of the plurality of energy ranges detected by the plurality of detectors in the presence of a substantially-unscattered gamma photon source.

5. A system according to claim 1,
wherein the acquired data representing true coincidences and scatter coincidences detected by the plurality of detectors comprises a sinogram,
wherein the sinogram is allocated into respective sinograms for each of the plurality of energy ranges, and
wherein the generated data representing expected true coincidences associated with each of the subset of the plurality of energy ranges comprise sinograms.

6. A system according to claim 1,
wherein the subset of the plurality of energy ranges are lower-energy energy ranges than other energy ranges of the plurality of energy ranges.

7. A system according to claim 1,
wherein the data representing true coincidences and scatter coincidences detected by the plurality of detectors includes time-of-flight data for each of the true coincidences and scatter coincidences, the processing unit to:
allocate the data into respective bins representing each of a plurality of time-of-flight ranges,
wherein the allocation of the data into respective ones of a plurality of energy ranges, the determination of the baseline response associated with each of the subset of the plurality of energy ranges, the generation of data representing expected true coincidences associated with each of the subset of the plurality of energy ranges, and the determination of a raw scatter estimate are performed for the data allocated into each of the respective bins.

8. A method comprising:
acquiring data representing true coincidences and scatter coincidences detected by a plurality of detectors;
allocating the data into respective ones of a plurality of energy ranges;
determining a baseline response associated with each of a subset of the plurality of energy ranges;
generating data representing expected true coincidences associated with each of the subset of the plurality of energy ranges based on the data allocated to each of the subset of the plurality of energy ranges and the baseline response associated with each of the subset of the plurality of energy ranges;
determining a raw scatter estimate based on the data representing expected true coincidences associated with each of the subset of the plurality of energy ranges and the data allocated to each of the subset of the plurality of energy ranges; and
reconstructing an image based on the raw scatter estimate and the data representing true coincidences and scatter coincidences.

9. A method according to claim 8, further comprising:
determining a high-energy scatter estimate based on data representing expected true coincidences associated with a highest-energy subset of the plurality of energy ranges and the data allocated to the highest-energy subset of the plurality of energy ranges,
wherein reconstructing the image comprises reconstruction of the image based on the raw scatter estimate, the high-energy scatter estimate, and the data representing true coincidences and scatter coincidences.

10. A method according to claim 9, further comprising
determining a corrected scatter estimate based on the raw scatter estimate and the high-energy scatter estimate; and
filtering the corrected scatter estimate,
wherein reconstructing the image comprises reconstruction of the image based on the filtered corrected scatter estimate and the data representing true coincidences and scatter coincidences.

11. A method according to claim 8, wherein the baseline response associated with each of the subset of the plurality of energy ranges comprises normalized counts of true coincidences for each of the subset of the plurality of energy ranges detected by the plurality of detectors in the presence of a substantially-unscattered gamma photon source.

12. A method according to claim 8,
wherein the acquired data representing true coincidences and scatter coincidences detected by the plurality of detectors comprises a sinogram,
wherein the sinogram is allocated into respective sinograms for each of the plurality of energy ranges, and
wherein the generated data representing expected true coincidences associated with each of the subset of the plurality of energy ranges comprise sinograms.

13. A method according to claim 8,
wherein the subset of the plurality of energy ranges are lower-energy energy ranges than other energy ranges of the plurality of energy ranges.

14. A method according to claim 8,
wherein the data representing true coincidences and scatter coincidences detected by the plurality of detectors includes time-of-flight data for each of the true coincidences and scatter coincidences, further comprising:
allocating the data into respective bins representing each of a plurality of time-of-flight ranges,
wherein the allocation of the data into respective ones of a plurality of energy ranges, the determination of the baseline response associated with each of the subset of the plurality of energy ranges, the generation of data representing expected true coincidences associated with each of the subset of the plurality of energy ranges, and the determination of a raw scatter estimate are performed for the data allocated into each of the respective bins.

15. A computer-readable medium storing processor-executable process steps executable by a processing unit to cause a system to:
acquire data representing true coincidences and scatter coincidences detected by a plurality of detectors;
allocate the data into respective ones of a plurality of energy ranges;
determine a baseline response associated with each of a subset of the plurality of energy ranges;
generate data representing expected true coincidences associated with each of the subset of the plurality of energy ranges based on the data allocated to each of the subset of the plurality of energy ranges and the baseline response associated with each of the subset of the plurality of energy ranges;
determine a raw scatter estimate based on the data representing expected true coincidences associated with each of the subset of the plurality of energy ranges and the data allocated to each of the subset of the plurality of energy ranges; and reconstruct an image based on the raw scatter estimate and the data representing true coincidences and scatter coincidences.

16. A medium according to claim 15, the processor-executable process steps executable by a processing unit to cause a system to:

determine a high-energy scatter estimate based on data representing expected true coincidences associated with a highest-energy subset of the plurality of energy ranges and the data allocated to the highest-energy subset of the plurality of energy ranges, wherein reconstruction of the image comprises reconstruction of the image based on the raw scatter estimate, the high-energy scatter estimate, and the data representing true coincidences and scatter coincidences.

17. A medium according to claim 16, the processor-executable process steps executable by a processing unit to cause a system to:

determine a corrected scatter estimate based on the raw scatter estimate and the high-energy scatter estimate; and filter the corrected scatter estimate, wherein reconstruction of the image comprises reconstruction of the image based on the filtered corrected scatter estimate and the data representing true coincidences and scatter coincidences.

18. A medium according to claim 15, wherein the baseline response associated with each of the subset of the plurality of energy ranges comprises normalized counts of true coincidences for each of the subset of the plurality of energy ranges detected by the plurality of detectors in the presence of a substantially-unscattered gamma photon source.

19. A medium according to claim 15, wherein the acquired data representing true coincidences and scatter coincidences detected by the plurality of detectors comprises a sinogram, wherein the sinogram is allocated into respective sinograms for each of the plurality of energy ranges, and wherein the generated data representing expected true coincidences associated with each of the subset of the plurality of energy ranges comprise sinograms.

20. A medium according to claim 15, wherein the data representing true coincidences and scatter coincidences detected by the plurality of detectors includes time-of-flight data for each of the true coincidences and scatter coincidences, the processor-executable process steps executable by a processing unit to cause a system to:

allocate the data into respective bins representing each of a plurality of time-of-flight ranges, wherein the allocation of the data into respective ones of a plurality of energy ranges, the determination of the baseline response associated with each of the subset of the plurality of energy ranges, the generation of data representing expected true coincidences associated with each of the subset of the plurality of energy ranges, and the determination of a raw scatter estimate are performed for the data allocated into each of the respective bins.

* * * * *